US011123214B2

United States Patent
Wilson et al.

(10) Patent No.: US 11,123,214 B2
(45) Date of Patent: Sep. 21, 2021

(54) BACK-BRACE ASSISTIVE DEVICE

(71) Applicants: Peter Wilson, Colorado Springs, CO (US); Van Wagner, Morrison, CO (US); Benjamin Topper, Colorado Springs, CO (US); Joshua Rands, Waconia, MN (US); Parker Steen, Westminster, CO (US)

(72) Inventors: Peter Wilson, Colorado Springs, CO (US); Van Wagner, Morrison, CO (US); Benjamin Topper, Colorado Springs, CO (US); Joshua Rands, Waconia, MN (US); Parker Steen, Westminster, CO (US)

( * ) Notice: Subject to any disclaimer, the term of this patent is extended or adjusted under 35 U.S.C. 154(b) by 401 days.

(21) Appl. No.: 16/058,079

(22) Filed: Aug. 8, 2018

(65) Prior Publication Data
US 2019/0076287 A1 Mar. 14, 2019

Related U.S. Application Data

(60) Provisional application No. 62/556,685, filed on Sep. 11, 2017.

(51) Int. Cl.
A61F 5/00 (2006.01)
A61F 5/02 (2006.01)
(52) U.S. Cl.
CPC .................. A61F 5/028 (2013.01)
(58) Field of Classification Search
USPC .......................................... 602/19
See application file for complete search history.

(56) References Cited

U.S. PATENT DOCUMENTS 1,316,915 A * 9/1919 Meyer et al. ........... A61F 5/028
602/19
3,889,664 A * 6/1975 Heuser .................... A61F 5/028
602/36
4,771,767 A * 9/1988 Steffee ............... A61B 17/7002
606/256

(Continued)

FOREIGN PATENT DOCUMENTS

AT          505853 A2 *  4/2009  ............. A61F 5/028
EP        2 062 487 A2    5/2009
WO       2016/076930 A1   5/2016

Primary Examiner — Kim M Lewis
(74) Attorney, Agent, or Firm — James A. Sheridan; Sheridan Law, LLC

(57) ABSTRACT

A back-brace assistive device is provided for supporting a proper lifting posture of a user, including a back-brace assembly featuring a series of interconnected and articulating vertebrae assemblies, as well as an upper back plate assembly and a lower back plate assembly, each in connection with the series of the vertebrae assemblies. Each vertebrae assembly fits into the adjacent assembly via a ball joint, and the series of the vertebrae assemblies couples with the upper and the lower back plate assemblies via additional ball joints. At least one support component extends from the upper back plate assembly, across the series of the articulating vertebrae assemblies, to the lower back plate assembly to provide rigidity and articulation support for the vertebrae assemblies. An anchoring mechanism such as a harness attaches to the back-brace assembly to secure the back-brace assembly to the user's back. Other embodiments are also disclosed.

20 Claims, 13 Drawing Sheets

(56) References Cited

U.S. PATENT DOCUMENTS

| | | | |
|---|---|---|---|
| 5,328,447 A | 7/1994 | Kapounek et al. | |
| 5,400,801 A | 3/1995 | Archer, III | |
| 5,540,688 A | 7/1996 | Navas | |
| 5,685,831 A * | 11/1997 | Floyd | A61F 5/026 2/45 |
| 5,768,717 A | 6/1998 | Le Sueur | |
| 5,840,051 A * | 11/1998 | Towsley | A61F 5/0125 602/19 |
| 6,280,405 B1 * | 8/2001 | Broselid | A61F 5/024 128/874 |
| 6,296,644 B1 * | 10/2001 | Saurat | A61B 17/7013 606/256 |
| 6,321,388 B1 | 11/2001 | Hildebrandt | |
| 6,687,920 B2 | 2/2004 | Berns | |
| 8,074,294 B2 | 12/2011 | Bowlus et al. | |
| 8,353,434 B2 | 1/2013 | Clayton, III et al. | |
| D699,364 S | 2/2014 | Chiang et al. | |
| 9,204,984 B2 | 12/2015 | Brown et al. | |
| 9,216,121 B2 * | 12/2015 | Galante | A61G 5/122 |
| 9,370,237 B2 | 6/2016 | Hiemenz et al. | |
| 9,504,307 B1 * | 11/2016 | Burnett | A45F 3/10 |
| 2002/0042584 A1 | 4/2002 | Rue | |
| 2003/0050581 A1 * | 3/2003 | Berns | A41D 13/0531 602/3 |
| 2004/0193085 A1 * | 9/2004 | Mazzarolo | A41D 13/0531 602/19 |
| 2005/0153153 A1 | 7/2005 | Saur et al. | |
| 2008/0021357 A1 * | 1/2008 | Firsov | A61F 5/026 602/19 |
| 2008/0228121 A1 * | 9/2008 | Hughes | A61F 5/026 602/35 |
| 2008/0301863 A1 | 12/2008 | Goff et al. | |
| 2009/0163841 A1 * | 6/2009 | Garth | A61F 5/028 602/19 |
| 2010/0088799 A1 | 4/2010 | Carter | |
| 2010/0204629 A1 * | 8/2010 | Specht | A61F 5/028 602/19 |
| 2010/0263111 A1 * | 10/2010 | Leatt | A42B 3/0473 224/271 |
| 2011/0167546 A1 | 7/2011 | Olson | |
| 2014/0012171 A1 | 1/2014 | Brown et al. | |
| 2014/0224849 A1 * | 8/2014 | Hiemenz | A42B 3/0473 224/271 |
| 2015/0164154 A1 * | 6/2015 | Bencini | A41D 13/0531 2/455 |
| 2015/0164171 A1 | 6/2015 | Margetis et al. | |
| 2016/0128861 A1 * | 5/2016 | Plaza | A61F 5/028 602/19 |

* cited by examiner

BACK-BRACE ASSISTIVE DEVICE

REFERENCE TO PENDING PRIOR PATENT APPLICATION

This application claims the benefit under 35 U.S.C. 119(e) of U.S. Provisional Patent Application No. 62/556,685, filed Sep. 11, 2017 by Peter Wilson, et al., for "BACK BRACE ASSISTIVE DEVICE," which patent application is hereby incorporated herein by reference.

BACKGROUND

Currently, existing back braces and/or harnesses are designed for positioning and fall-arrest purposes during climbing, construction, and other recreational and/or industrial activities. These assistive devices do not simultaneously provide posture support in addition to their primary positioning and fall-arrest purposes. Conversely, existing back supports are designed to assist the wearer during lifting or other activities by transferring support, for example, from the lower back to the abdominal cavity, to enable the user to lift heavier weight. Other back supports brace the lumbar spine or provide spinal decompression.

Existing back braces and other devices fail to provide any type of simple, adjustable, and effective mechanism for preventing and/or correcting poor bodily form in a manner that supports the entire spinal column during nearly all ranges of motion, including proper lifting form.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a back-brace assistive device. The back-brace assistive device may include a back-brace assembly having (a) a series of interconnected vertebrae assemblies; (b) an upper back plate assembly coupled with the series of the vertebrae assemblies; (c) a lower back plate assembly coupled with the series of the vertebrae assemblies, wherein a plurality of ball joints interconnect the series of the vertebrae assemblies with one another, with the upper back plate assembly, and with the lower back plate assembly; and (d) at least one support component extending from the upper back plate assembly, across each of the vertebrae assemblies, to the lower back plate assembly. The back-brace assistive device may also include an anchoring mechanism attached to the back-brace assembly, the anchoring mechanism configured to secure the series of the vertebrae assemblies against a spine of a user.

Another embodiment provides a system for assisting lifting movements of a user. The system may include a back-brace assembly including: (a) an articulating series of vertebrae connected between an upper back plate assembly and a lower back plate assembly; (b) a plurality of rotational joints, one of the plurality of the rotational joints positioned between each of the vertebrae, between the upper back plate assembly and an adjacent one of the vertebrae, and between the lower back plate assembly and an adjacent one of the vertebrae; and (c) two opposing support components, each extending from a first end affixed to the upper back plate assembly, through the series of the vertebrae, to a second end affixed to the lower back plate assembly, wherein when the back-brace assembly is secured along a spine of the user, a bending of the spine causes the two opposing support components to deform elastically along with the spine and to articulate each of the vertebrae relative to one another, thereby supporting a healthy lifting posture and distributing a lifting force across a substantial portion of a back of the user.

Yet another embodiment provides a method of supporting a proper lifting posture. The method may include the steps of (1) providing a back-brace assistive device comprising a back-brace assembly affixed to an anchoring mechanism configured to secure the back-brace assembly to a user's back, the back-brace assembly including: (a) a plurality of articulating vertebrae assemblies rotationally coupled between an upper back plate assembly and a lower back plate assembly; and (b) at least one support component extending from a first end affixed to the upper back plate assembly, through the plurality of the articulating vertebrae assemblies, to a second end affixed to the lower back plate assembly; (2) adjusting the back-brace assembly to fit a length of the user's back; (3) securing the back-brace assembly to the user's back via the anchoring mechanism; and (4) lifting, by the user, an object using the proper lifting posture supported by the back-brace assembly.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Embodiments disclosed herein involve a back-brace assistive device used, in some embodiments, in conjunction with a harness system. As discussed above in the Background section, existing back-brace devices are primarily designed for positioning and fall assistance or prevention during various sporting or industrial activities (e.g., Exofit "exoskeleton" braces), or alternatively, they provide support transfer between various areas of the back and core to provide lift assistance and/or enable the user to lift heavier weight, rather than enforcing proper lifting form.

Embodiments of the disclosed back-brace assistive device support the user's back in a manner that encourages proper form and movement for nearly all ranges of motion, including during lifting and other activities. Embodiments employ a series of vertebrae that are interconnected through a series of ball joints, as well as one or more elastically deforming support components that connect each of the vertebrae between an upper back plate and a lower back plate to provide reinforcement and stiffness to the vertebrae. The vertebra allow the support components to evenly distribute force over the user's entire back, or at least over 75-percent of the spinal column from the lower back to the upper back. The disclosed back-brace assistive device provides a simple and light-weight design that requires neither hydraulics nor robotics.

Figure 1:
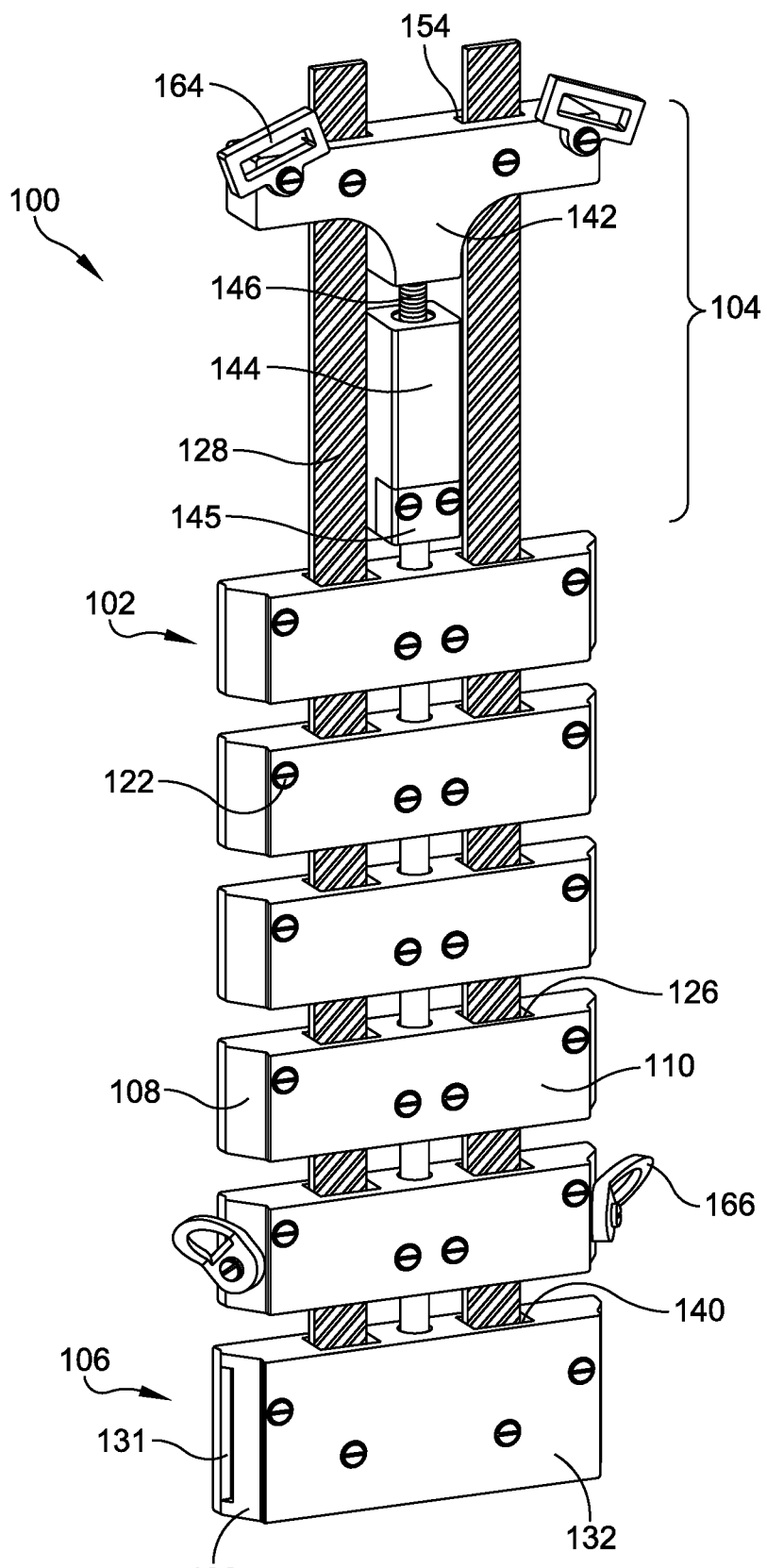
FIG. 1 illustrates a perspective view of a back-brace assembly for securing along a user's spine.
Figure 2:
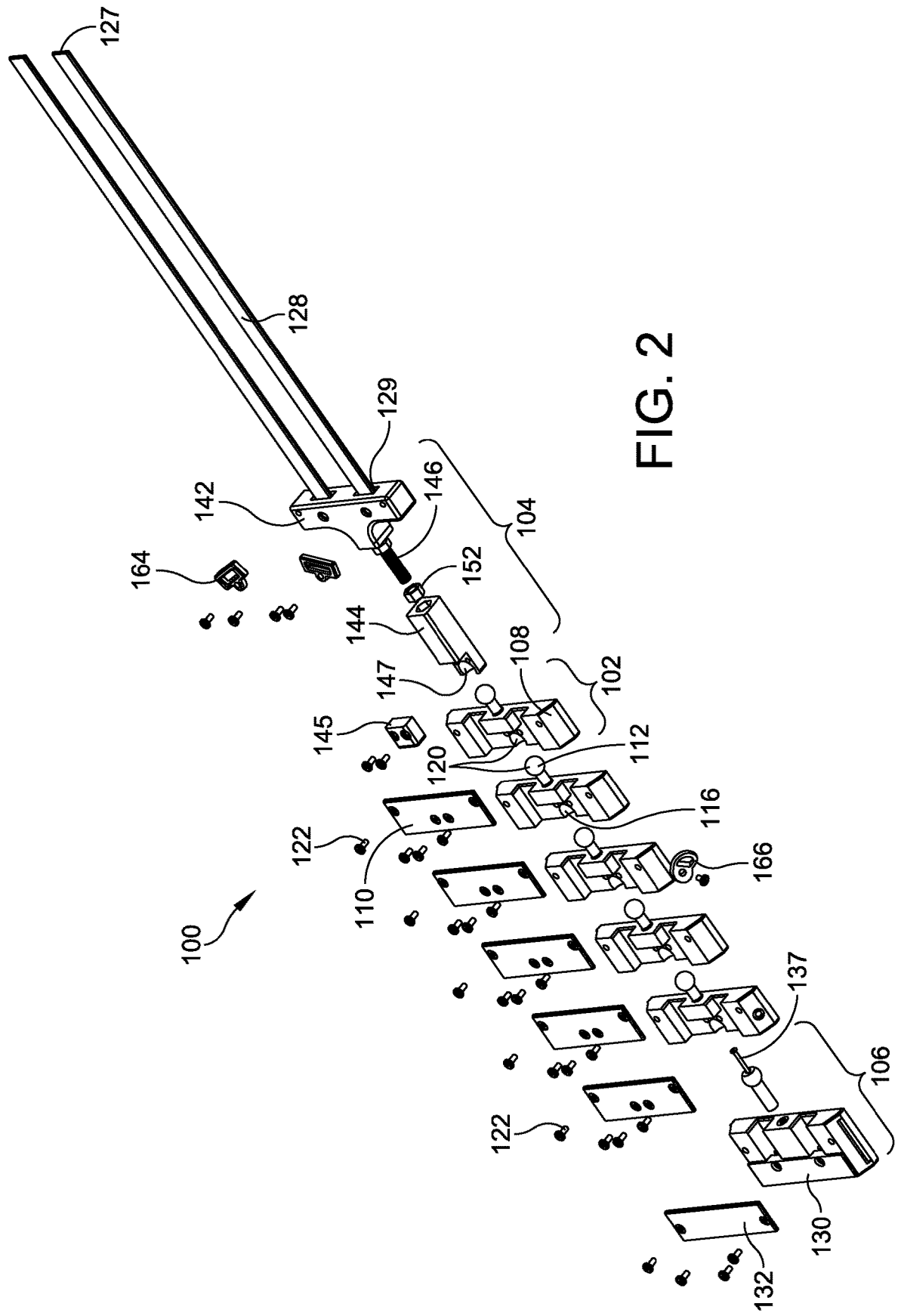
FIG. 2 illustrates an exploded view of the back-brace assembly of FIG. 1.

Turning to the figures, FIGS. 1-2 illustrate perspective and exploded views of one embodiment of a back-brace assembly 100, respectively. In this embodiment, the back-brace assembly 100 may include a series of interconnected vertebrae assemblies 102, which connect to each other and to an upper back plate assembly 104 and a lower back plate assembly 106 through a plurality of rotative ball joints 120. Two support components 128 provide another, reinforcing connection between the upper back plate assembly 104, each of the vertebrae assemblies 102, and the lower back plate assembly 106, as detailed further below.

Figure 3:
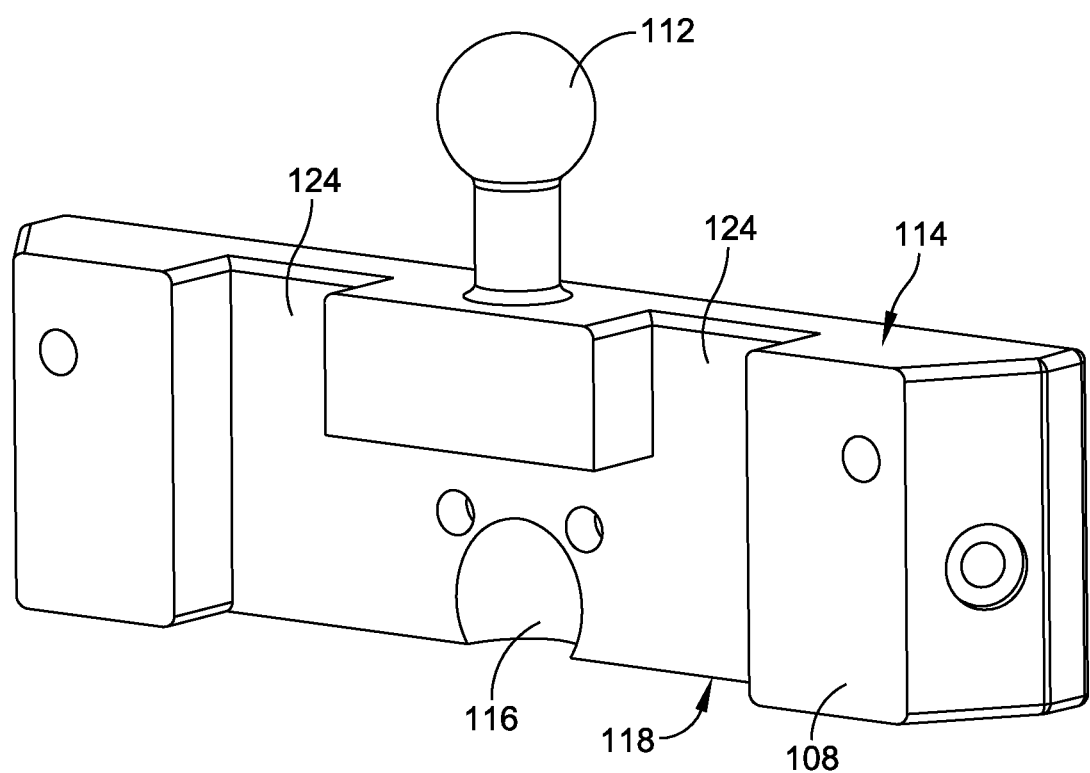
FIG. 3 illustrates a perspective view of one embodiment of a vertebrae body of the back-brace assembly of FIG. 1.
Figure 4:
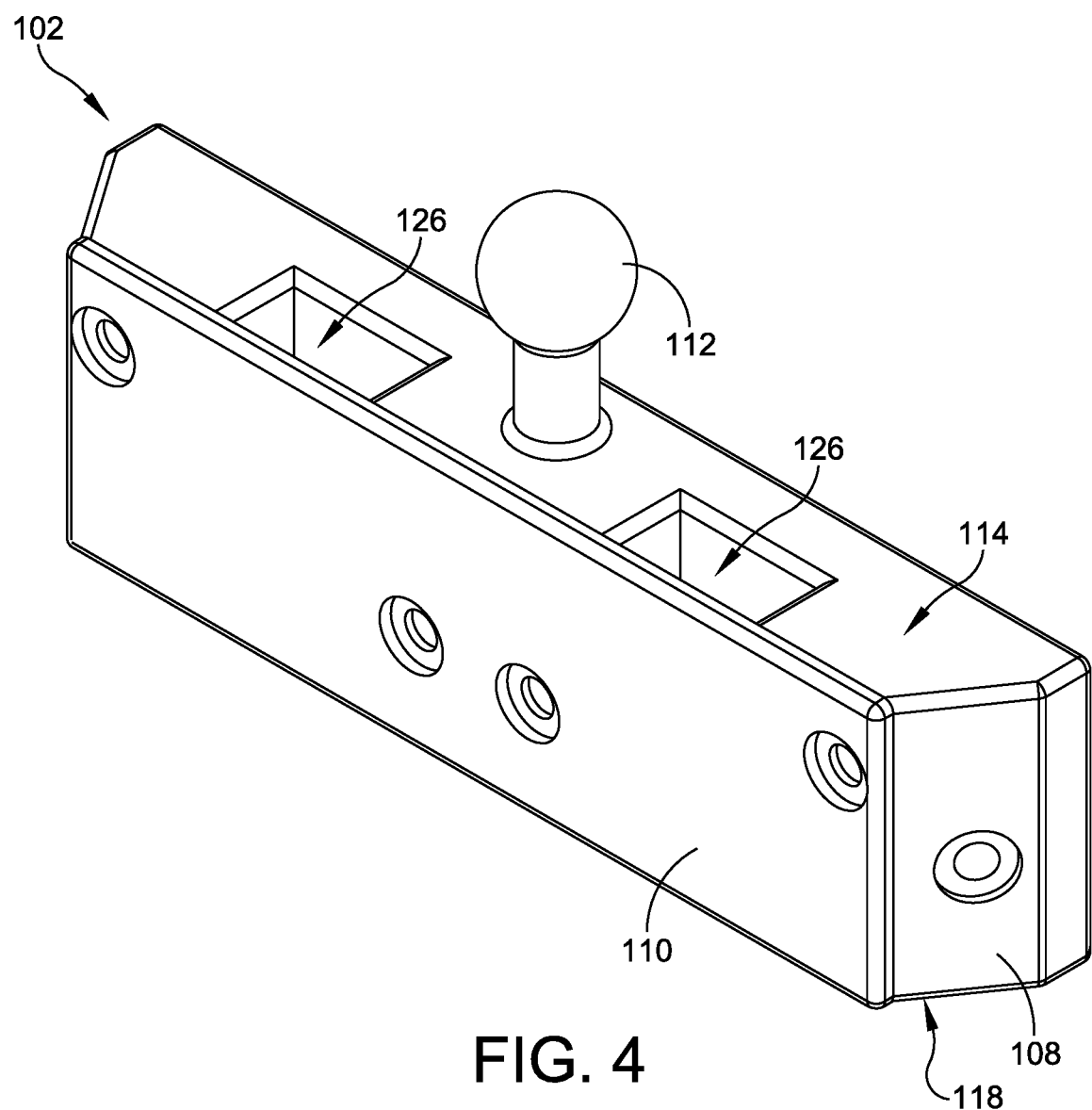
FIG. 4 illustrates a perspective view of one embodiment of a vertebrae assembly incorporating the vertebrae body of FIG. 3.

The vertebrae assemblies 102 serve to distribute force over a region or an entirety the user's back. Each of the vertebrae assemblies 102 may include a vertebrae body 108 and an attached vertebrae cover 110. FIGS. 3-4 illustrate respective perspective views of one embodiment of the vertebrae body 108 and the vertebrae assembly 102, in which the cover 110 is fastened to the body 108. In one embodiment, the vertebrae body 108 may include a spherical bearing 112 protruding outward from a top end 114 of the body 108. A bottom end 118 of the body 108 may form a semi-spherical socket 116. As shown in the exploded view of FIG. 2, the spherical bearing 112 is configured to nest and rotate within the semi-spherical socket 116 formed within the adjacent vertebrae body 108, thereby forming the ball joint 120 between each vertebrae assembly 102 when the cover 110 is attached to the vertebrae body 108 via one or more fasteners 122. Each of the ball joints 120 allow for free rotation of the spherical bearings 112 within two simultaneous planes at any one time, while preventing translation in any direction. In this regard, the ball joints 120 provide a limited range of smooth movement in all directions.

In this embodiment, each of the vertebrae bodies may also include a pair of notches 124. When the cover 110 is attached to form the vertebrae assembly 102, as shown in FIG. 4, the notches 124 combine with the cover 110 to form a pair of support channels 126, each configured to receive the support component 128 therethrough, as detailed further below.

Figure 5:
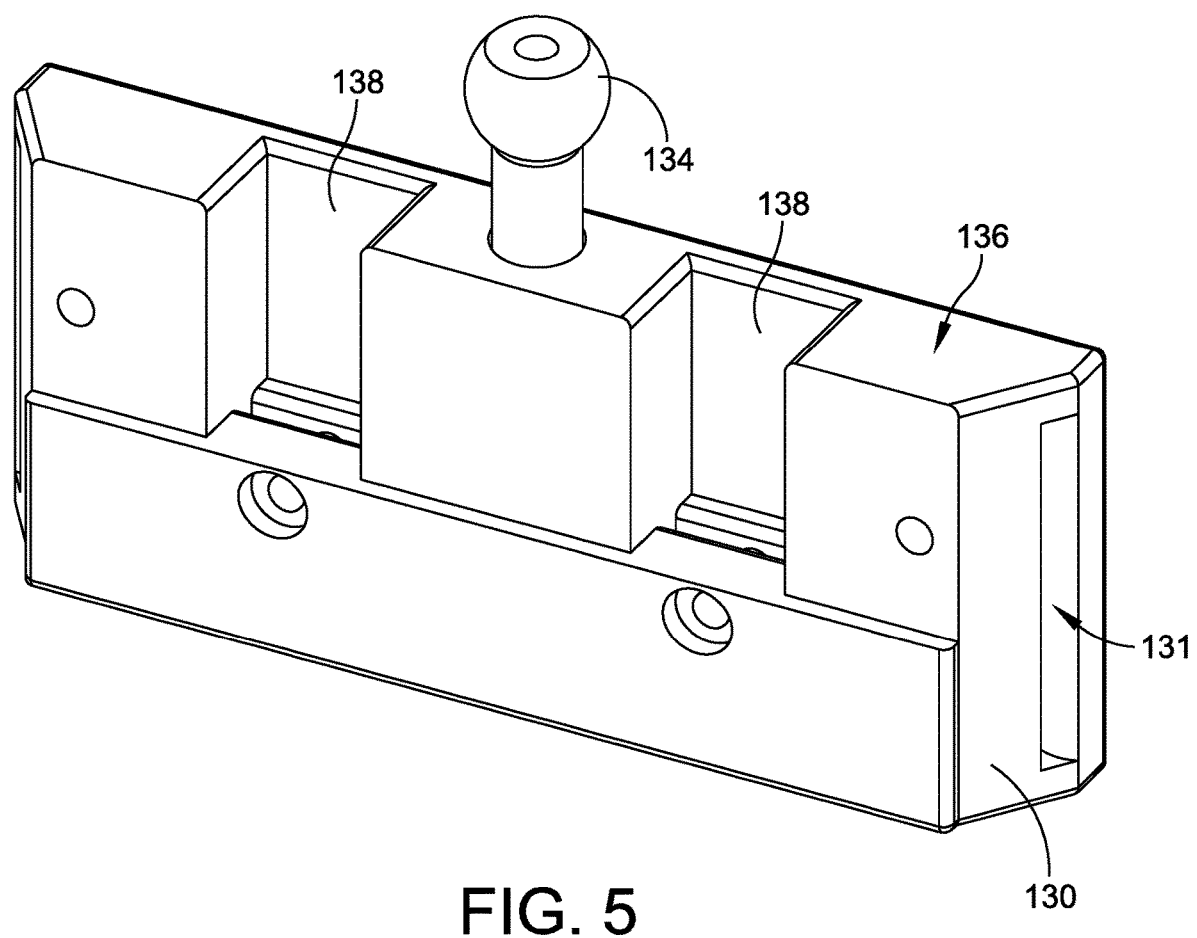
FIG. 5 illustrates a perspective view of one embodiment of a lower back plate of the back-brace assembly of FIG. 1.
Figure 6:
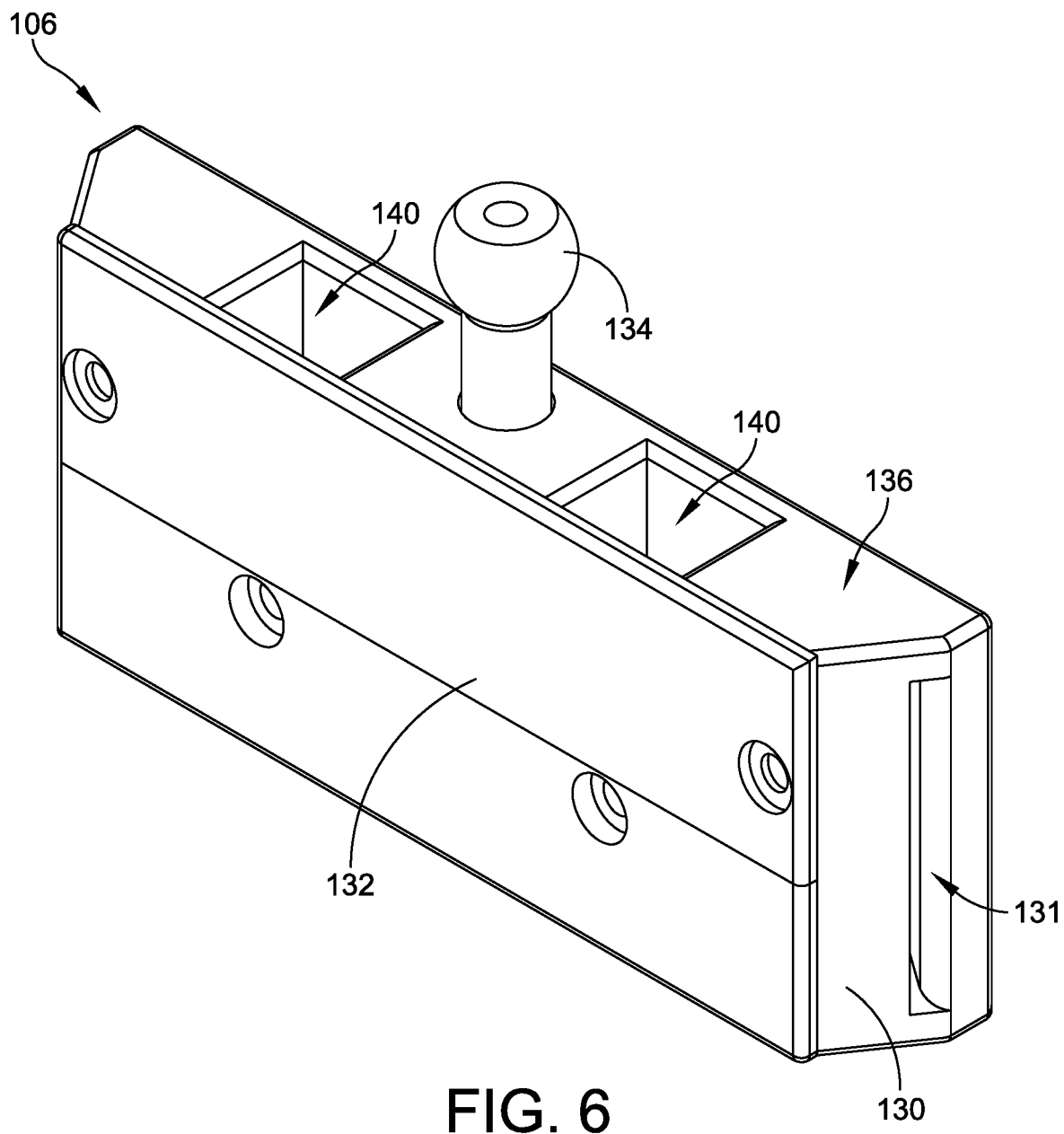
FIG. 6 illustrates a perspective view of one embodiment of a lower back plate assembly incorporating the lower back plate of FIG. 5.

As shown in FIGS. 1-2 and as discussed above, the series of vertebrae assemblies 102 couples with the lower back plate assembly 106. This connection occurs via an additional ball joint 120 between the lower back plate assembly 106 and the adjacent vertebrae assembly 102. More specifically, and in one embodiment, the lower back plate assembly 106 may include a lower back plate 130, shown in FIG. 5, having an attached lower back plate cover 132, as shown in FIG. 6. Similar to the vertebrae body 108, a spherical bearing 134 may protrude from a top end 136 of the lower back plate 130. The spherical bearing 134 may be attached in any appropriate manner, including being screwed into the back plate with an appropriate fastener 137, as shown in FIG. 2, or molded or otherwise formed in place as part of the lower back plate 130 itself. A belt aperture 131 may also be formed transversely across and through the lower back plate 130. The belt aperture 131 may be configured to receive an attachment belt, discussed further below in relation to FIG. 9.

Also similar to the vertebrae body 108, the lower back plate 130 may include a pair of notches 138 that combine with the lower back plate cover 132 to form a pair of support channels 140 when the cover 130 is attached to the plate 130, as shown in FIG. 6. The support channels 140 may each be sized to receive one of the support components 128 (FIGS. 1-2) such that a lower end 129 of each of the support components 128 may be secured within the support channels 140 at the lower back plate assembly 106, as discussed below.

Figure 7:
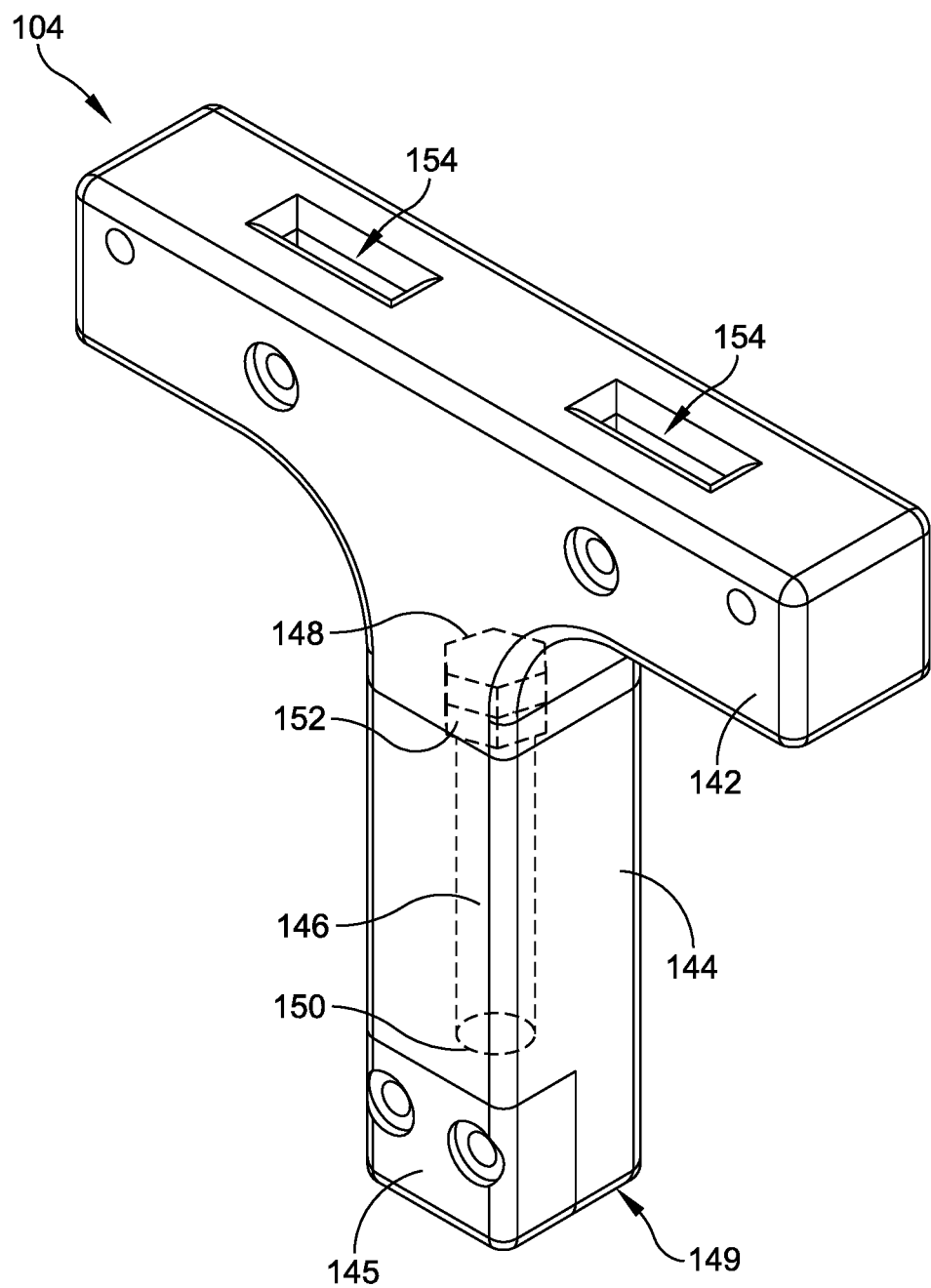
FIG. 7 illustrates a perspective view of one embodiment of an upper back plate assembly of the back-brace assembly of FIG. 1.
Figure 8:
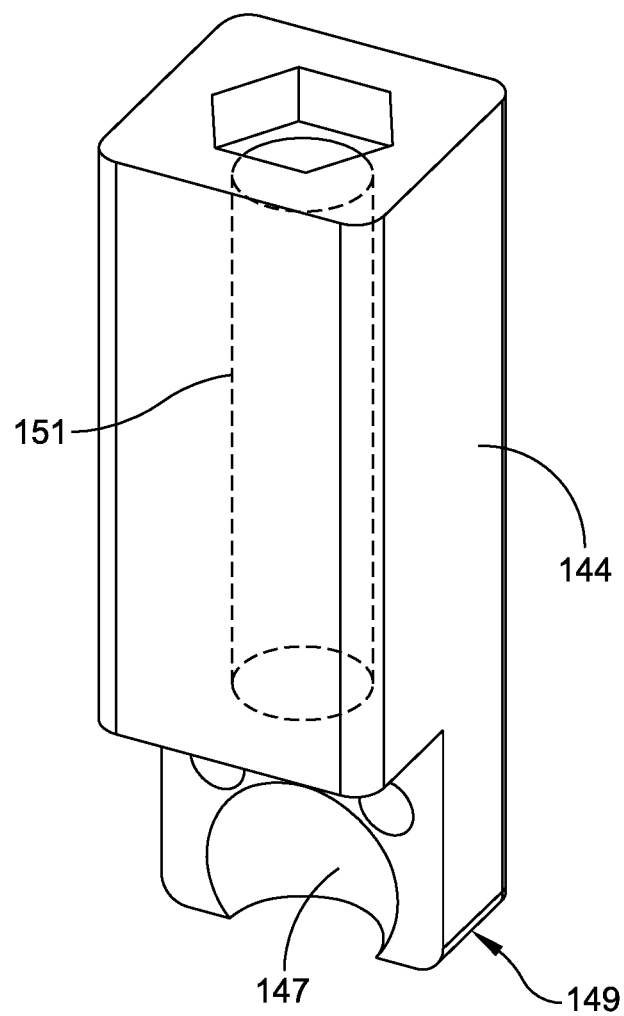
FIG. 8 illustrates a perspective view of one embodiment of an upper body of the upper back plate assembly of FIG. 7.

The series of vertebrae assemblies 102 may also couple with the upper back plate assembly 104. This coupling may occur via another ball joint 120 between the top vertebrae assembly 102 and the upper back plate assembly 104, as shown in FIGS. 1-2. FIG. 7 illustrates a perspective view of one embodiment of the upper back plate assembly 104. In this embodiment, the upper back plate assembly 104 may include an upper head 142, an upper body 144, and an upper cover 145. As shown in FIG. 2, the spherical bearing 112 extending from the adjacent vertebrae assembly 102 may nest within a semi-spherical socket 147 formed in a lower end 149 of the upper body 144 (FIG. 8), and be held in position by the upper cover 145.

Figure 9:
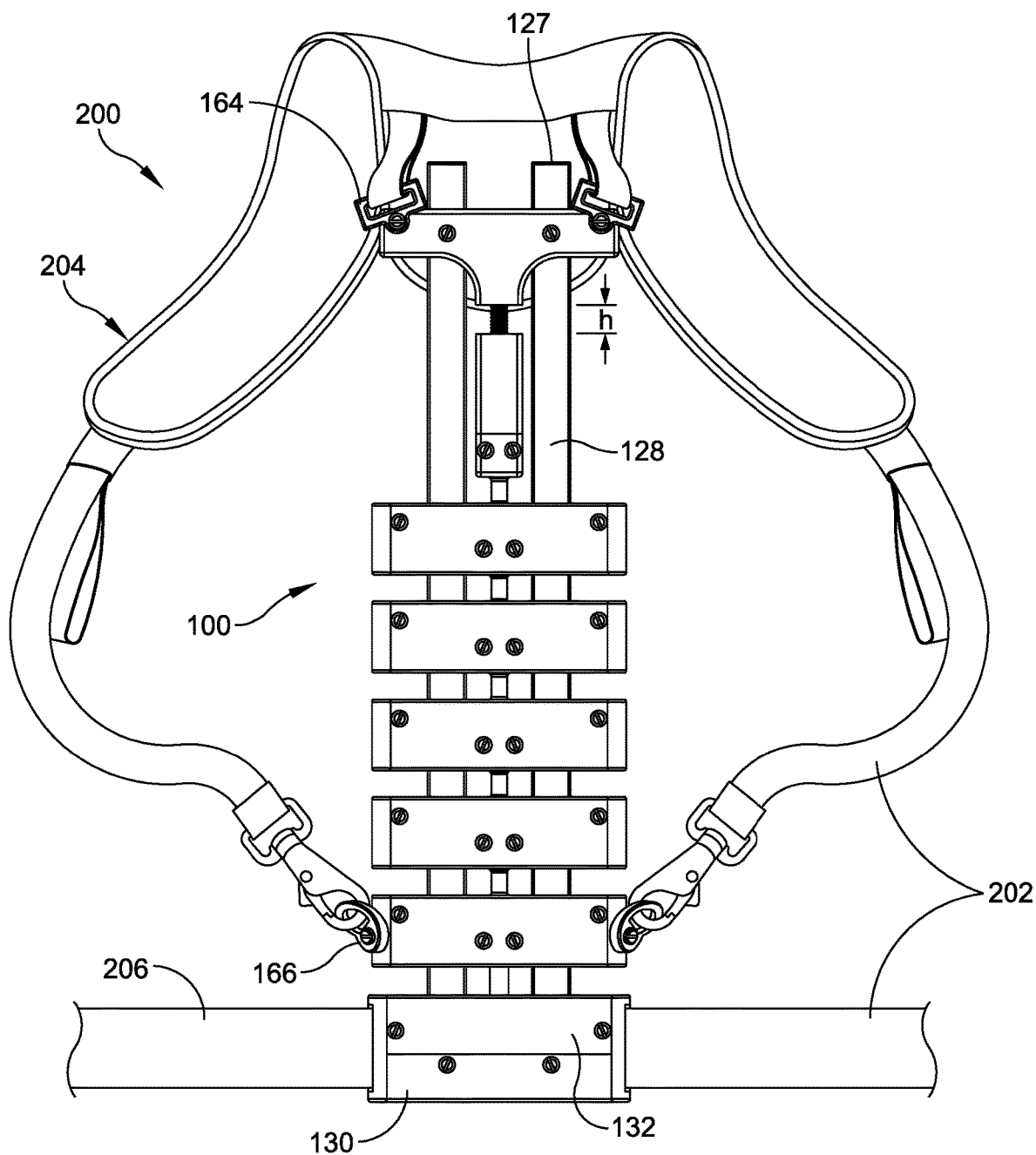
FIG. 9 illustrates a top plan view of one embodiment of a back-brace assistive device including the back-brace assembly of FIG. 1, as attached to a two-part harness system for securing the back-brace assembly to a user's back.
Figure 10:
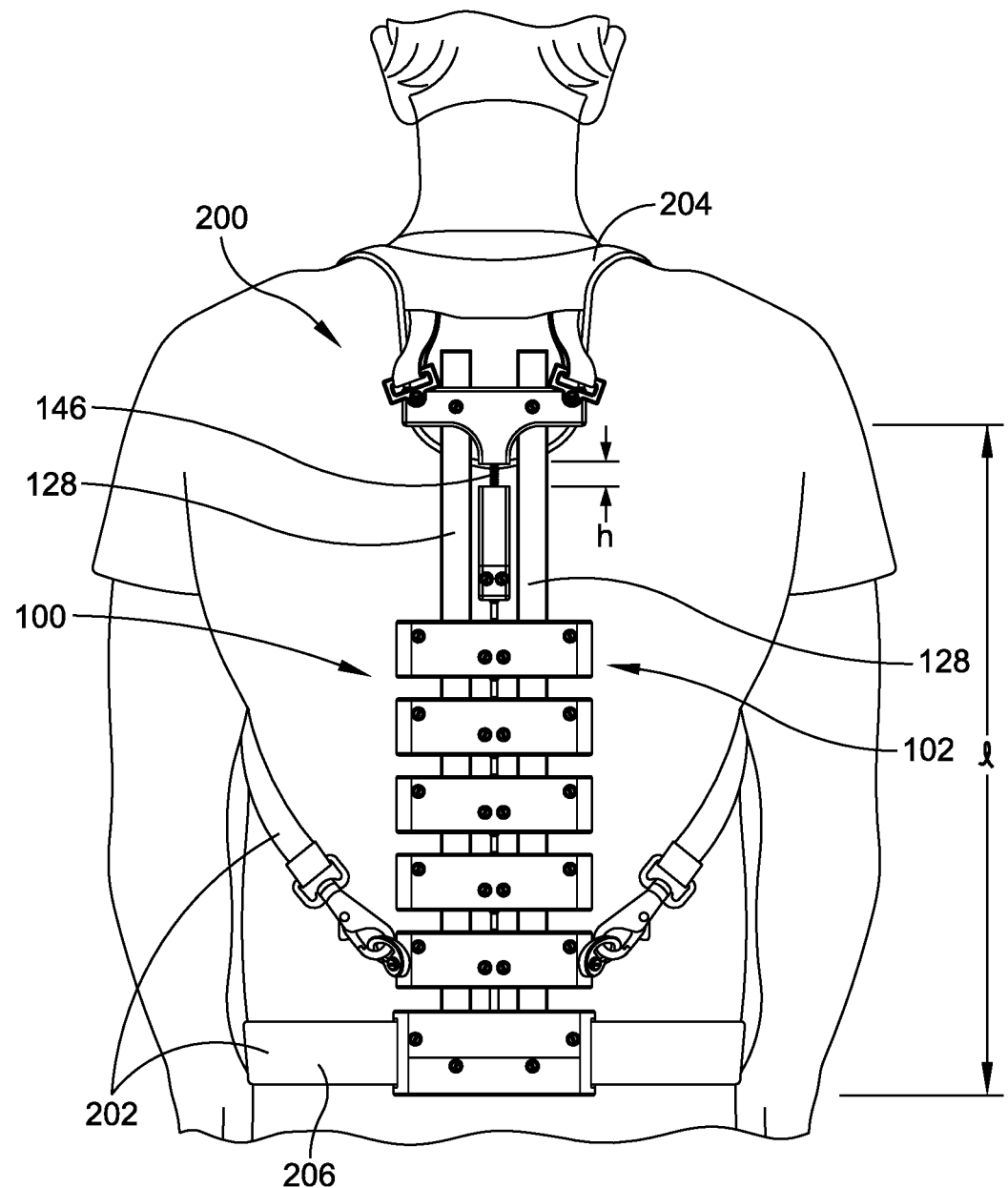
FIG. 10 illustrates a top plan view of the back-brace assistive device of FIG. 9, as secured to a user's back.

In one embodiment, the upper back plate assembly 104 may provide telescoping adjustment for fine tuning the overall length of the back-brace assembly 100. That is, the upper head 142 may be adjustably attached to the upper body 144 via a fine-tune adjustment bolt 146. In some embodiments, the fine-tune adjustment bolt 146 may be have a top end 148 that is affixed within the upper head 142 such that a bottom end 150 of the adjustment bolt 146 may be threaded directly into a threaded aperture 151 of the upper body 144, shown in FIG. 8, or into a nut 152 countersunk within the upper body 144, as shown in FIGS. 2 and 7. By rotating the upper head 142, a user may adjust the adjustment bolt 146 upward or downward to position the upper head 142 at a desired height, h, above the upper body 144, as shown in FIG. 9. In this manner, the user may adjust the back-brace assembly 100 to fit the user's particular physiology, or to fit a length, l, between the user's hips and shoulder blades, as shown in FIG. 10. In other embodiments, the adjustment bolt 146 may be threadably engaged with the upper head 142 and/or the upper body 144 in any appropriate manner that allows for rotation of the bolt 146 to increase and/or decrease the height, h, of the upper head 142 relative to the upper body 144.

The upper head 142 may form two support channels 154 that align with the support channels 126 of each of the vertebrae assemblies 102 and the support channels 140 of the lower back plate assembly 106. One of the support components 128 may be inserted into the support channels 154, 126, and 140 on each opposing side of the series of the ball joints 120, where the lower end 129 of each of the support components 128 may be pinch or press secured within the support channels 140 of the lower back plate assembly 106 via one or more rotational fasteners 122 (e.g. screws) and an upper end 127 of each of the support components 128 may be pinch or press secured within the support channels 154 of the upper head 142 via one or more rotational fasteners 122, as shown in FIGS. 1-2.

The rigid support components 128 provide common components that connect each of the vertebrae assemblies 102 to both the lower back plate assembly 106 the upper back plate assembly 104, thereby stiffening the series of vertebrae assemblies 102 such that they cannot rotate completely freely on the ball joints 120 and enabling the individual vertebrae assemblies 102 to evenly distribute force over the majority or an entirety of the user's back. In this embodiment, the support components 128 may be carbon fiber bars that provide resistance to both forward bending (flexion) and torsional bending, but that elastically deform in those and other directions and return to their original form after deformation. In other embodiments, the support components may be springs, rods, strips, bungee cords, or any appropriate elastic material that returns to its original shape after deformation. The support components 128 may feature a low profile that doesn't interfere with other components or the wearer. In one embodiment, the support components 128 may be attached to the user's back without the vertebrae assemblies, which may provide a thermally cooler and more lightweight system.

FIG. 9 illustrates a top plan view of one embodiment of a back-brace assistive device 200. In this embodiment, the back-brace assistive device 200 may incorporate the back-brace assembly 100, detailed above, attached to an anchoring mechanism for securing or anchoring the back-brace assembly 100 to the user's back along the user's spine. In this embodiment, the anchoring mechanism may comprise a two-part harness 202 having a set of shoulder straps 204 and a belt 206. The shoulder straps 204 may connect to the back-brace assembly 100 via a pair of upper strap anchors 164 affixed, for example, to the upper back plate assembly 104 and a pair of lower clip anchors 166 affixed to, for example, the lowermost vertebrae assembly 102, as shown. The upper strap anchors 164 and the lower clip anchors 166 may have any appropriate size, shape, type, and/or configuration and may be attached to any appropriate component of the back-brace assembly 100. Moreover, the upper strap anchors 164 and the lower clip anchors 166 may be attached at any appropriate position to any appropriate component of the back-brace assembly 100.

In this embodiment, the separate belt 206 of the harness system 202 may be threaded through the belt aperture 131 formed transversely within the lower back plate 130 such that the belt 206 may be cinched about the wearer's hips. The two-part harness system 202, including the shoulder straps 204 and the belt 206 may include any appropriate existing shoulder straps and/or belt, saving the user the expense of purchasing a new or a custom harness. Alternatively, the straps and/or the belt may be custom made for the wearer and/or the particular assembly. The shoulder strap portion 204 may feature adjustable straps that fit in a manner that retains each of the vertebrae assemblies 102 flush against the user's spine during wear.

Notably, embodiments of the anchoring mechanism or harness system 202 may include any appropriate mechanism for securing the back-brace assembly 100 to the user's back. The harness may be attached to the assembly 100, as discussed above, or it may be built directly into the assembly 100. The harness may be a two-piece shoulder strap/belt combination, or it may be a single unit that functions similar to a backpack. The upper back brace assembly 104, the vertebrae assemblies 102, and the lower back brace assembly 106 may feature any appropriate modifications and/or configurations to accommodate the structure of the anchoring mechanism.

FIG. 10 illustrates one embodiment of the back-brace assistive device 200, as secured to a wearer's back via the harness 202. To achieve an optimal fit, as shown, the user may elect to use any appropriate number of vertebrae assemblies 102 to accommodate the length, l, of the wearer's torso. In this regard, the user may attach a customized number of the vertebrae assemblies 102 to the support components 128 in order to accommodate the user's height/torso length. The user may then fine tune the height of the upper back plate assembly 102 by adjusting the height, h, of the adjustment bolt 146 as discussed above in relation to FIGS. 7-8. Through these macro and micro adjustments, the back-brace assembly 100 is able to accommodate different body types.

Figure 11A:
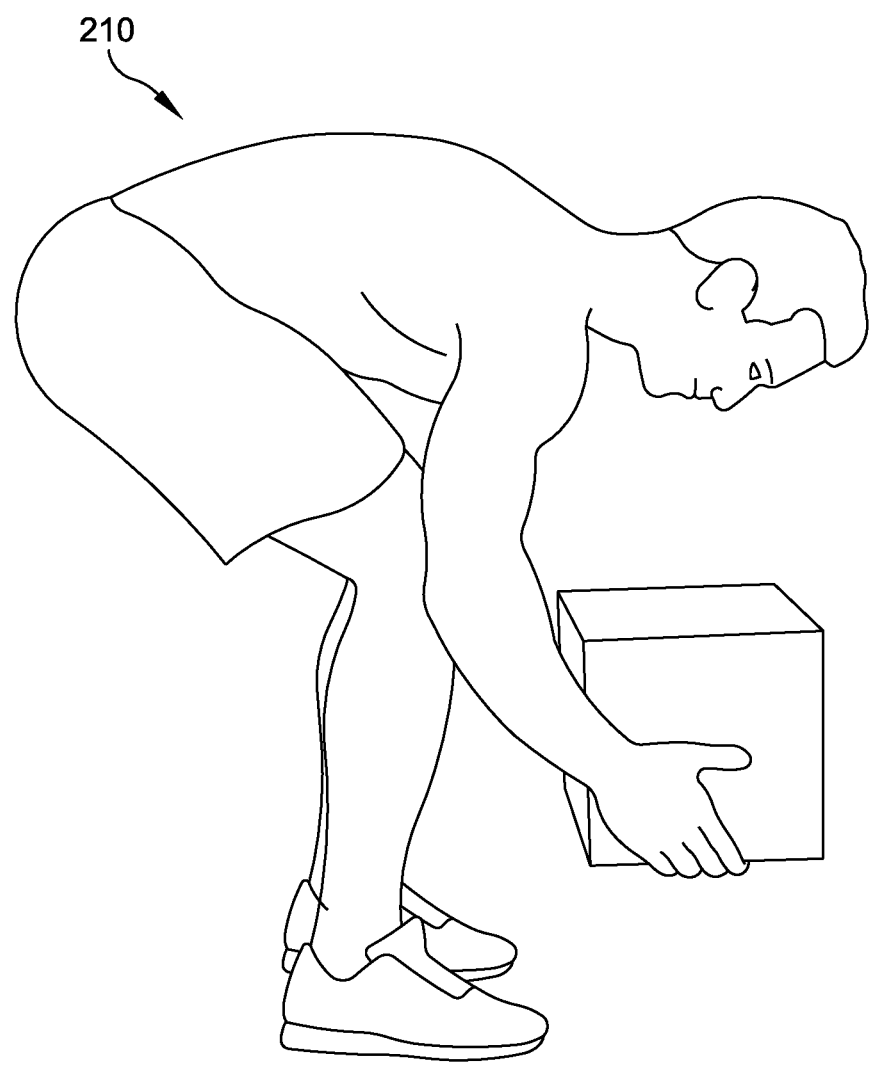
FIGS. 11A-11B provide exemplary illustrations of lifting biomechanics with bad lifting form and proper lifting form, respectively.
Figure 11B:
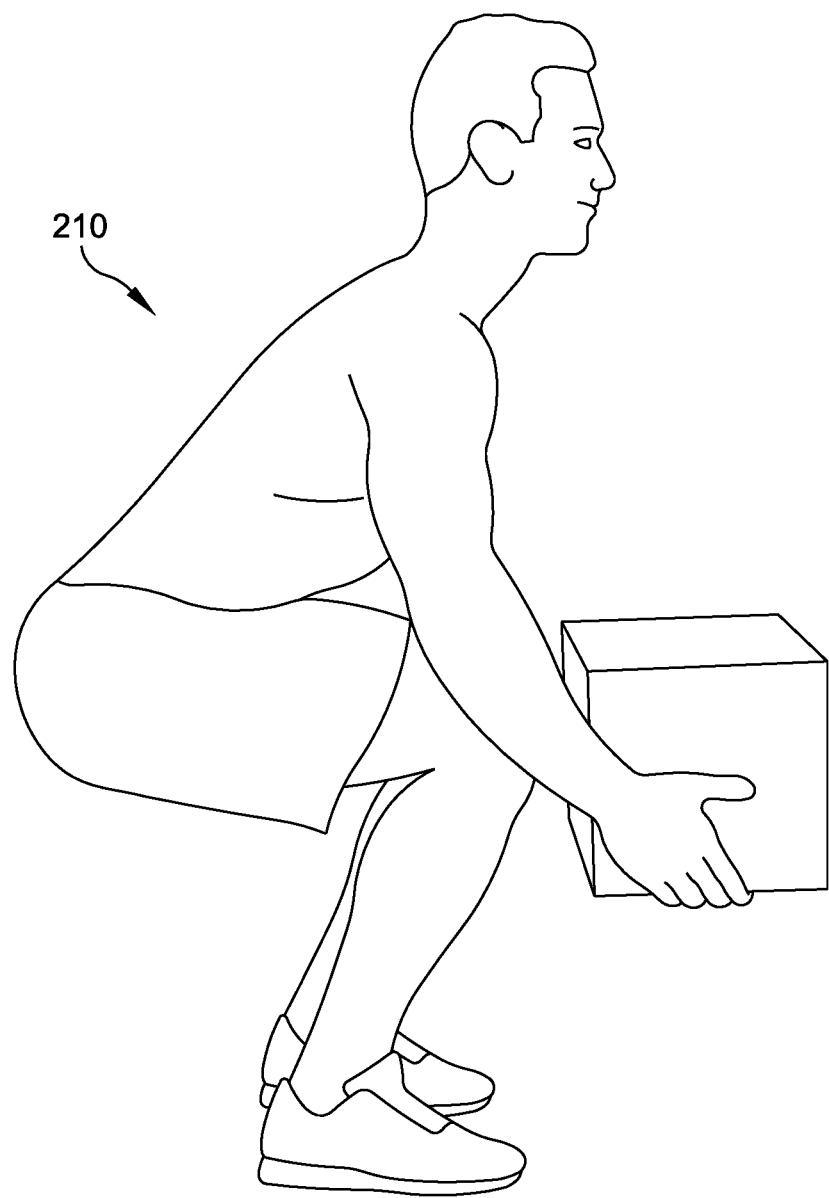

FIGS. 11A-11B illustrate the posture assistance provided by embodiments of the back-brace assistive device 200 to a person 210, as described above. Specifically, FIG. 11A provides an exemplary illustration of improper lifting biomechanics, or bad lifting form, while FIG. 11B provides an exemplary illustration of lifting biomechanics with a more proper form, as is encouraged and supported by the disclosed back-brace assistive device 200. That is, in use, the user may bend over to pick an object up. As the user begins to arch his or her back, the ball joints 120 enable the vertebrae assemblies 102 to articulate and closely approximate the user's movement, while the connected and rigid support components 128 flex elastically to curve only slightly with the user's spine/back to encourage the user's back to remain flat, as shown in FIG. 11B, thereby resisting the overly flexed and unhealthy arching motion shown in FIG. 11A, as well as providing lift assistance as the rigid support components 128 also provide sufficient torsional resistance to twisting and arching to encourage proper lifting form. Once the user returns to his or her original position, the elastic support components 128 return to their initial position and no longer have an effect upon the user when the back is no longer arched.

Similarly, if the user tries to lift an object such as a heavy box using only his or her core/lower back, the support components 128, in preventing the back from over-arching, encourage the user to bend down with his or her legs and use the entire body, not just the back. Finally, if the user is moving a heavy object from side to side by rotating only his or her torso, the series of vertebrae assemblies 102 combined with the support components 128 threaded therethrough, or the vertebrae system, discourages that twisting movement and instead encourages the user to move his or her entire body, not just his or her back. In this regard, the back-brace assembly provides support for nearly all ranges of motion. The device 200 may be used for additional support, encouraging proper form, and injury prevention in a variety of movement contexts, including mining, construction, forestry, warehousing, moving, residential work, and even military use. The device 200 or the back-brace assembly 100 without the harness 202, may also be used for rehabilitation purposes in the medical field.

Embodiments of the back-brace assistive device 200 provide lift assistance and posture support without the use of electronic and/or hydraulic components. In some embodiments, the back-brace assembly 100 may be used without the harness 202. For example, the back-brace assembly 100, including the interconnected vertebrae assemblies 102 and the support components 128, may be attached through a vest such as, for instance, a Kevlar vest typically worn by peace officers. In another embodiment, the harness 202 may be replaced with another component configured to secure to the back-brace assembly 100 to the user. For example, the assembly 100 may attach via a wearable fabric such as a fitted or structured shirt with hook-and-loop fastener patches (e.g., VELCRO® Brand hook and loop patches) to secure the back-brace assembly 100 along the user's spine.

Components of the back-brace assembly 100, including the vertebrae, the upper back plate, and the lower back plate assemblies 102, 104, 106, respectively, may be formed of any appropriately robust, lightweight polymer such as, for example, carbon fiber, Teflon, or any appropriate material that may be compression and injection molded, rendering the assembly lightweight in comparison to the user's other clothing and/or gear. In one embodiment, the back-brace assembly 100 may have a weight of no more than 15 pounds. In other embodiments, the assembly may weigh 5 pounds or less. The back-brace assembly 100 is also economical, as manufacturing using compression molding is relatively inexpensive and accessible, with low barriers to entry.

In one embodiment, the ball joints 120 may comprise a low-friction material, which allows the ball joints 120 to move with ease. In addition, any component that contacts the wearer when in use may be lined with memory foam such that the component provides both comfort and an optimal fit. The memory foam may be attached to the components using an adhesive, via one or more fasteners, or in any other appropriate fashion such as, for example, via VELCRO® Brand hook and loop fasteners.

In various embodiments, the back-brace assistive device 200 incorporates a variety of easily replaceable components. If one component is damaged or worn, it may be replaced without the need to replace the entire assembly. The use of high-strength, minimal, and replaceable components renders the system strong, durable, reliable, easy to assemble, and easy to maintain.

Figure 12:
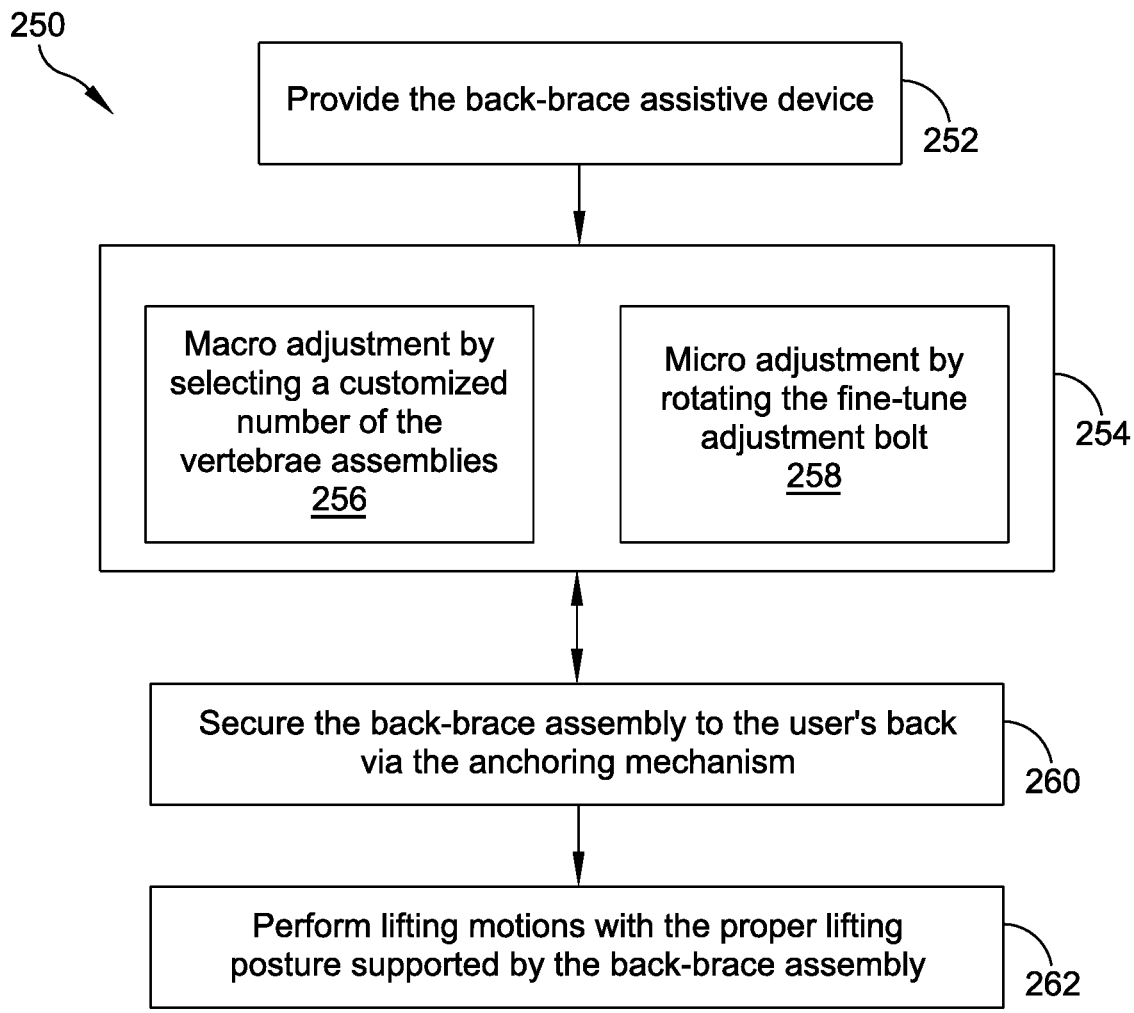
FIG. 12 provides a flowchart depicting an exemplary method of lifting an object with proper lifting form, as supported by the back-brace assistive device of FIGS. 9-10.

FIG. 12 provides a flowchart depicting an exemplary method (250) of using the back-brace assistive device 200 to support proper lifting form. In this embodiment, the method (250) begins with providing an embodiment of the back-brace assistive device (252), as described above. The user may then adjust the back-brace assembly 100 to fit the length, l, between the user's hips and shoulder blades, as shown in FIG. 10 (254). In this regard, the user may initially select a customized number of the articulating vertebrae assemblies 102 to include in the series of the vertebrae assemblies for a macro adjustment (256). For instance, a shorter user may select fewer vertebrae assemblies 102, while a taller user may select additional vertebrae assemblies 102 to stack or include in the series of the vertebrae assemblies 102 between the lower back plate assembly 106 and the upper back plate assembly 104. The user may then fine tune the adjustment using the adjustment bolt 146 (258) to increase the height, h, of the upper head 142 above the upper body 144, as shown in FIG. 9. Once the back-brace assembly 100 has been adjusted to fit the user (254), the back-brace assembly 100 may be secured to the user's back via the anchoring mechanism (260), or in this embodiment, via the harness 202 including the shoulder straps 204 and the belt 206. In one embodiment, the micro adjustment (258) may occur after the back-brace assembly is secured to the user's back. Once the assembly 100 is secured, the user may engage in lifting motions (262) using a proper lifting posture as supported by the back-brace assembly 100.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A back-brace assistive device, comprising:
   a back-brace assembly having:
      a series of interconnected vertebrae assemblies;
      an upper back plate assembly coupled with the series of the interconnected vertebrae assemblies;
      a lower back plate assembly coupled with the series of the interconnected vertebrae assemblies, wherein a plurality of ball joints interconnect the series of the interconnected vertebrae assemblies with one another, with the upper back plate assembly, and with the lower back plate assembly; and
      at least one support component extending from the upper back plate assembly, across each of the vertebrae assemblies, to the lower back plate assembly; and
   an anchoring mechanism attached to the back-brace assembly, the anchoring mechanism configured to secure the series of the interconnected vertebrae assemblies against a spine of a user.

2. The back-brace assistive device of claim 1, wherein:
   each of the vertebrae assemblies comprises a vertebrae body and a vertebrae cover, the vertebrae body having an upper end and a lower end;
   a spherical bearing protrudes from the upper end;
   a semi-spherical socket is formed in the lower end; and
   when the vertebrae covers are attached to the vertebrae bodies, the spherical bearings are rotationally captured within the semi-spherical sockets of adjacent ones of the vertebrae bodies to form the plurality of the ball joints.

3. The back-brace assistive device of claim 2, wherein each of the ball joints enables a range of rotational motion approximating an entire range of motion of the user.

4. The back-brace assistive device of claim 1, wherein the at least one support component comprises two carbon fiber bars positioned on opposing sides of the plurality of the ball joints, wherein the two carbon fiber bars deform elastically with an articulation of the series of the interconnected vertebrae assemblies in response to a bending of the user's spine.

5. The back-brace assistive device of claim 4, wherein the two carbon fiber bars resist forward bending and torsional bending.

6. The back-brace assistive device of claim 1, wherein the back-brace assembly configured to extend over at least 75 percent of the user's spine.

7. The back-brace assistive device of claim 1, wherein:
one or more of the vertebrae assemblies are removable to adjust a height of the back-brace assembly to match a length of the user's torso; and
the upper back plate assembly comprises an upper head rotationally coupled with an upper body via a fine-tune adjustment bolt, wherein rotating the fine-tune adjustment bolt increases an offset between the upper head and the upper body to further adjust the height of the back-brace assembly to match the length of the user's torso.

8. The back-brace assistive device of claim 1, wherein the anchoring mechanism comprises a two-part harness comprising:
a pair of shoulder straps attached to the upper back plate assembly and one of the vertebrae assemblies; and
a belt coupled to the lower back plate assembly.

9. The back-brace assistive device of claim 1, wherein the back-brace assembly is configured to provide posture support during lifting motions without an electronic or a hydraulic component.

10. The back-brace assistive device of claim 1, further comprising one or more memory foam components, each configured to line an interface between the back-brace assembly and a back of the user.

11. A system for assisting lifting movements of a user, comprising:
a back-brace assembly including:
an articulating series of vertebrae connected between an upper back plate assembly and a lower back plate assembly;
a plurality of rotational joints, one of the plurality of the rotational joints positioned between each of the vertebrae, between the upper back plate assembly and an adjacent one of the vertebrae, and between the lower back plate assembly and an adjacent one of the vertebrae; and
two opposing support components, each extending from a first end affixed to the upper back plate assembly, through the series of the vertebrae, to a second end affixed to the lower back plate assembly, wherein when the back-brace assembly is secured along a spine of the user, a forward bending of the spine causes the two opposing support components to deform elastically along with the spine and to articulate each of the vertebrae relative to one another, thereby supporting a healthy lifting posture and distributing a lifting force across a substantial portion of a back of the user.

12. The system of claim 11, wherein the plurality of the rotational joints comprises a plurality of ball joints.

13. The system of claim 11, wherein each of the opposing support components comprises a carbon fiber bar that resists the forward bending of the spine.

14. The system of claim 11, wherein the series of the vertebrae includes a customized number of vertebrae assemblies, and wherein the customized number of the vertebrae assemblies is selected based on a length of a torso of the user.

15. The system of claim 14, wherein the upper back plate assembly comprises an upper head, an upper body, and an adjustment bolt threadably engaged therebetween, and wherein rotation of the adjustment bolt alters a distance between the upper head and the upper body to micro adjust the back-brace assembly based on the length of the user's torso.

16. The system of claim 11, further comprising an anchoring mechanism configured to secure the back-brace assembly to the user's back.

17. The system of claim 16, wherein the anchoring mechanism comprises a harness system.

18. The system of claim 17, wherein the harness system comprises a two-part harness including:
a set of shoulder straps attached to the upper back plate assembly and a select one of the vertebrae; and
a belt attached to the lower back plate assembly.

19. A method of supporting a proper lifting posture, comprising:
providing a back-brace assistive device comprising a back-brace assembly affixed to an anchoring mechanism configured to secure the back-brace assembly to a user's back, the back-brace assembly including:
a plurality of articulating vertebrae assemblies rotationally coupled between an upper back plate assembly and a lower back plate assembly; and
at least one support component extending from a first end affixed to the upper back plate assembly, through the plurality of the articulating vertebrae assemblies, to a second end affixed to the lower back plate assembly;
adjusting the back-brace assembly to fit a length of the user's back;
securing the back-brace assembly to the user's back via the anchoring mechanism; and
lifting, by the user, an object using the proper lifting posture supported by the back-brace assembly.

20. The system of claim 19, wherein the adjusting the back-brace assembly comprises:
selecting a customized number of the plurality of the articulating vertebrae assemblies to be rotationally coupled between the upper back plate assembly and the lower back plate assembly; and
rotating an adjustment bolt of the upper back plate assembly to adjust a height of the upper back plate assembly.

* * * * *